US007875453B2

(12) United States Patent
Collins

(10) Patent No.: US 7,875,453 B2
(45) Date of Patent: Jan. 25, 2011

(54) DIFFERENTIATION OF MULTI-LINEAGE PROGENITOR CELLS TO HEPATOCYTES

(75) Inventor: Daniel P. Collins, Lino Lakes, MN (US)

(73) Assignee: BioE LLC, St. Paul, MN (US)

( * ) Notice: Subject to any disclaimer, the term of this patent is extended or adjusted under 35 U.S.C. 154(b) by 118 days.

(21) Appl. No.: 11/452,502

(22) Filed: Jun. 14, 2006

(65) Prior Publication Data

US 2007/0292398 A1 Dec. 20, 2007

(51) Int. Cl.
C12N 5/071 (2010.01)
C12N 5/00 (2006.01)
C12N 5/02 (2006.01)
(52) U.S. Cl. ..................... 435/377; 435/372
(58) Field of Classification Search .................. None
See application file for complete search history.

(56) References Cited

U.S. PATENT DOCUMENTS

| | | | |
|---|---|---|---|
| 5,486,359 | A | 1/1996 | Caplan et al. |
| 5,624,840 | A | 4/1997 | Naughton et al. |
| 6,967,086 | B2 | 11/2005 | Guarino et al. |
| 2002/0027233 | A1 | 3/2002 | Yamaki et al. |
| 2002/0164794 | A1 | 11/2002 | Wernet |
| 2003/0235563 | A1* | 12/2003 | Strom et al. ............. 424/93.21 |
| 2004/0107453 | A1 | 6/2004 | Furcht et al. |
| 2005/0255592 | A1* | 11/2005 | Collins et al. ............... 435/372 |
| 2006/0040392 | A1 | 2/2006 | Collins et al. |
| 2006/0182724 | A1* | 8/2006 | Riordan ..................... 424/93.7 |

FOREIGN PATENT DOCUMENTS

| | | |
|---|---|---|
| WO | WO 90/11354 | 10/1990 |
| WO | WO 91/01140 | 2/1991 |
| WO | WO 93/04169 | 3/1993 |

OTHER PUBLICATIONS

BD™ Biosciences Technical Bulletin BD™ Three Dimensional Collagen Composite and OPLA Scaffolds, 2002.*
Evarts et al. Cancer Res. 49:1541-1547; 1989.*
Bigbee et al., "Monoclonal antibodies specific for the M- and N-forms of human glycophorin A*," *Molecular Immunology*, 1983, 20(12):1353-1362.
Bradley, "Modifying the mammalian genome by gene targeting," *Curr. Opin. Biotechnol.*, 1991, 2:823-829.
Cole et al., "The EBV-Hybridoma Technique and its Application to Human Lung Cancer," *Monoclonal Antibodies and Cancer Therapy*, Alan R. Liss, Inc., 1985, pp. 77-96.
Cote et al., "Generation of human monoclonal antibodies reactive with cellular antigens," *Proc. Natl. Acad. Sci. USA*, 1983, 80:2026-2030.

Eggens et al., "Specific Interaction between $Le^x$ and $Le^x$ Determinants," *J. Biol. Chem.*, 1989, 264(16):9476-9484.
Forraz et al., "Characterization of a Lineage-Negative Stem-Progenitor Cell Population Optimized for Ex Vivo Expansion and Enriched for LTC-IC," *Stem Cells*, 2004, 22:100-108.
Fowler and Greenspan, "Application of Nile Red, a Fluorescent Hydrophobic Probe, for the Detection of Neutral Lipid Deposits in Tissue Sections: Comparison with Oil Red $O^1$," *J. Histochem. Cytochem.*, 1985, 33(8):833-836.
Jaiswal et al., "Osteogenic Differentiation of Purified, Culture-Expanded Human Mesenchymal Stem Cells In Vitro," *J. Cell. Biochem.*, 1997, 64(2):295-312.
Jennings et al., "P4.1 CD9 cluster workshop report: cell surface binding and functional analysis," *Leukocyte Typing V*, Schlossman et al. (eds.), 1995, pp. 1249-1251.
Kannagi et al., "A Series of Human Erythrocyte Glycosphingolipids Reacting to the Monoclonal Antibody Directed to a Developmentally Regulated Antigen, SSEA-1," *J. Biol. Chem.*, 1982, 257(24):14865-14874.
Kay et al., "Gene therapy," *Proc. Natl. Acad. Sci. USA*, 1997, 94:12744-12746.
Köhler et al., "Continuous cultures of fused cells secreting antibody of predefined specificity," *Nature*, 1975, 256:495-497.
Kozbor and Roder, "The production of monoclonal antibodies from human lymphocytes," *Immunology Today*, 1983, 4:72-79.
Lanza et al., "cDNA Cloning and Expression of Platelet p24/CD9," *J. Biol. Chem.*, 1991, 266(16):10638-10645.
Magnani et al., "Monoclonal Antibodies PMN 6, PMN 29, and PM-81 Bind Differently to Glycolipids Containing a Sugar Sequence Occurring in Lacto-$N$-Fucopentaose III," *Arch. Biochem. Biophys.*, 1984, 233(2):501-506.
Outram et al., "Erythromyeloid lineage fidelity is conserved in erythroleukaemia," *Leuk. Res.*, 1988, 12(8):651-657.
Pittenger et al., "Multilineage Potential of Adult Human Mesenchymal Stem Cells," *Science*, 1999, 284:143-147.
Rubinstein et al., "Anti-Platelet Antibody Interactions with Fcγ Receptor," *Seminars in Thrombosis and Hemostatis*, 1995, 21:10-22.
Solter and Knowles, "Monoclonal antibody defining a stage-specific mouse embryonic antigen (SSEA-1)," *Proc. Natl. Acad. Sci. USA*, 1978, 75(11):5565-5569.
Telen and Bolk, "Human red cell antigens. IV. The abnormal sialoglycoprotein of Gerbich-negative red cells," *Transfusion*, 1987, 27:309-314.
Thomas and Capecchi, "Site-Directed Mutagenesis by Gene Targeting in Mouse Embryo-Derived Stem Cells," *Cell*, 1987, 51:503-512.
Von dem Borne and Modderman, "P2.1 Cluster report: CD9," *Leukocyte Typing IV*, 1989, Knapp et al. (eds.), pp. 989-990.
Wright and Tomlinson, "The ins and outs of the transmembrane 4 superfamily," *Immunology Today*, 1994, 15(12):588-594.
"BD™ Three Dimensional Collagen Composite and OPLA® Scaffolds," BD Biosciences, 2002, 4 pages.

* cited by examiner

*Primary Examiner*—Joanne Hama
(74) *Attorney, Agent, or Firm*—Fish & Richardson P.C.

(57) ABSTRACT

Fetal blood multi-lineage progenitor cells that are capable of a wide spectrum of transdifferentiation are described, as well as methods of differentiating the progenitor cells into mature hepatocytes.

6 Claims, 2 Drawing Sheets

FIG 2
FIG 2A
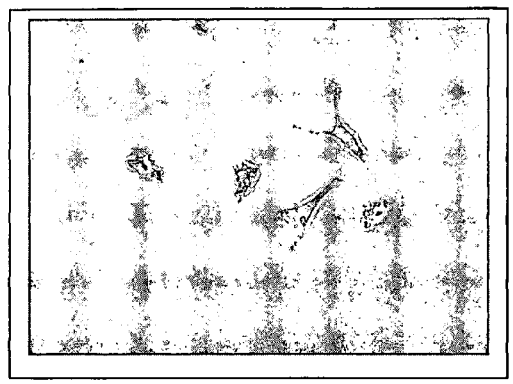
FIG 2B
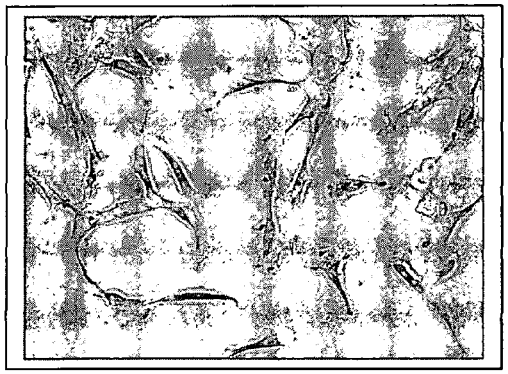
FIG 2C
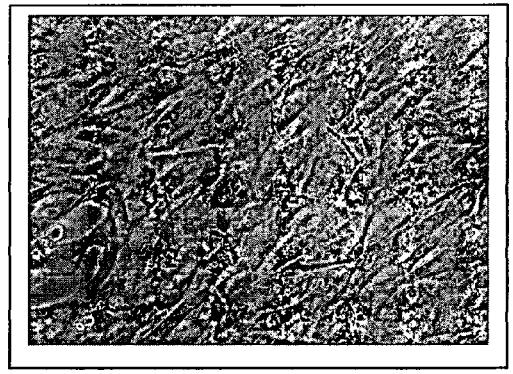
FIG 2D

DIFFERENTIATION OF MULTI-LINEAGE PROGENITOR CELLS TO HEPATOCYTES

TECHNICAL FIELD

The invention relates to mature hepatocytes, and more particularly, to differentiating multi-lineage progenitor cells (MLPC) from human blood to mature hepatocytes, and producing clonal populations of mature hepatocytes from clonal MLPC lines.

BACKGROUND

Progenitor cells capable of hematopoietic reconstitution after myeloablative therapy have been identified in a number of sources including the bone marrow, umbilical cord and placental blood, and in the peripheral blood of subjects treated with stem cell-mobilizing doses of granulocyte-colony stimulation factor. These cells, often referred to as hematopoietic stem cells (HSC), are identified by the presence of cell surface glycoproteins such as CD34 and CD133. HSC represent a very small percentage of the total population of cells given as part of a 'bone marrow transplant' and are considered to be the life-saving therapeutic portion of this treatment responsible for the restoration of the blood-forming capacity of patients given myeloablative doses of chemotherapy or radiation therapy. Stem cell therapies via bone marrow transplantation have become a standard treatment for a number of intractable leukemias and genetic blood disorders.

Recent studies have suggested the presence of a more primitive cell population in the bone marrow capable of self-renewal as well as differentiation into a number of different tissue types other than blood cells. These multi-potential cells were discovered as a minor component in the CD34-plastic-adherent cell population of adult bone marrow, and are variously referred to as mesenchymal stem cells (MSC) (Pittenger, et al., *Science* 284:143-147 (1999)) or multi-potent adult progenitor cells (MAPC) cells (Furcht, L. T., et al., U.S. patent publication 20040107453 A1). MSC cells do not have a single specific identifying marker, but have been shown to be positive for a number of markers, including CD29, CD90, CD105, and CD73, and negative for other markers, including CD14, CD3, and CD34. Various groups have reported to differentiate MSC cells into myocytes, neurons, pancreatic beta-cells, liver cells, bone cells, and connective tissue. Another group (Wernet et al., U.S. patent publication 20020164794 A1) has described an unrestricted somatic stem cell (USSC) with multi-potential capacity that is derived from a $CD45^-/CD34^-$ population within cord blood.

SUMMARY

The invention is based on the discovery that mature hepatocytes can be obtained by inducing differentiation of multi-lineage progenitor cells (MLPC) from human fetal blood. As described herein, fetal blood MLPC are distinguished from bone marrow-derived MSC, HSC, and USSC on the basis of their immunophenotypic characteristics, gene expression profile, morphology, and distinct growth pattern. The invention provides methods for developing monotypic clonal cell lines from individual cells and clonal populations of mature hepatocytes derived from such clonal cell lines. The invention also provides methods for cryopreserving MLPC (e.g., for cord blood banking) and mature hepatocytes.

In one aspect, the invention features a composition that includes a purified population of human fetal blood multi-lineage progenitor cells (MLPC) or a clonal line of human fetal blood MLPC, a differentiation medium effective to induce differentiation of the MLPC into cells having a mature hepatocyte phenotype, and a three-dimensional scaffold, wherein the MLPC are positive for CD9, negative for CD45, negative for CD34, and negative for SSEA-4. The differentiation medium can include ascorbic acid, hydrocortisone, transferrin, insulin, epidermal growth factor, hepatocyte growth factor, fibroblast growth factor-basic, fibroblast growth factor-4, and stem cell factor. The three-dimensional scaffold can include collagen or can be coated with collagen.

The invention also features a method of producing a population of cells having a mature hepatocyte phenotype. The method includes a) providing a three-dimensional scaffold housing a purified population of MLPC or a clonal line of MLPC; b) culturing the purified population of MLPC or the clonal line of MLPC with a differentiation medium effective to induce differentiation of the MLPC into cells having the mature hepatocyte phenotype, wherein the MLPC are positive for CD9, negative for CD45, negative for CD34, and negative for SSEA-4. The differentiation medium can include ascorbic acid, hydrocortisone, transferrin, insulin, epidermal growth factor, hepatocyte growth factor, fibroblast growth factor-basic, fibroblast growth factor-4, and stem cell factor. The three-dimensional scaffold can include collagen or can be coated with collagen. The method further can include testing the cells having the mature hepatocyte phenotype for intracellular serum albumin or hepatocyte growth factor receptor, and/or testing the cells for intracellular insulin or intracellular proinsulin.

In another aspect, the invention features a method for producing a population of cells having a mature hepatocyte phenotype from human fetal blood. The method includes contacting a human fetal blood sample with a composition including dextran; anti-glycophorin A antibody; anti-CD15 antibody; and anti-CD9 antibody; allowing the sample to partition into an agglutinate and a supernatant phase; recovering cells from the supernatant phase; purifying MLPC from the recovered cells by adherence to a solid substrate, wherein the MLPC are positive for CD9 and positive for CD45; culturing the MLPC such that the MLPC obtain a fibroblast morphology; loading the MLPC having the fibroblast morphology, or progeny thereof, into a three-dimensional scaffold to form a loaded scaffold; and culturing the loaded scaffold with a differentiation medium effective to induce differentiation of the MLPC into cells having the mature hepatocyte phenotype. The method further can include producing a clonal line of MLPC from the MLPC having the fibroblast morphology before loading the three-dimensional scaffold.

In yet another aspect, the invention features a clonal population of mature hepatocytes and compositions containing such clonal populations. In one embodiment, a composition includes a clonal population of mature hepatocytes and a culture medium. The clonal population of mature hepatocytes can be housed within a three-dimensional scaffold (e.g., a three-dimensional scaffold including collagen or coated with collagen). Such compositions further can include a cryopreservative (e.g., dimethylsulfoxide (DMSO) such as 1 to 10% DMSO). The cryopreservative can be fetal bovine serum, human serum, or human serum albumin in combination with one or more of the following: DMSO, trehalose, and dextran. For example, the cryopreservative can be human serum, DMSO, and trehalose, or fetal bovine serum and DMSO.

The invention also features an article of manufacture that includes a clonal population of mature hepatocytes. The clonal population can be housed within a container (e.g., a vial or a bag). The container further can include a cryopreservative. The clonal population can be housed within a three-dimensional scaffold. The three-dimensional scaffold can be housed within a well of a multi-well plate.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 2A-2D are photomicrographs depicting the morphology of developing MLPC. FIG. 2A shows an early culture of MLPC isolated from umbilical cord blood demonstrating the cells in the leukocyte morphology phase. FIG. 2B shows a culture of MLPC beginning to change their morphology from leukocyte to fibroblast morphology. FIG. 2C shows a later culture of MLPC in logarithmic growth phase. FIG. 2D shows a fully confluent culture of MLPC.

DETAILED DESCRIPTION

Figure 1:
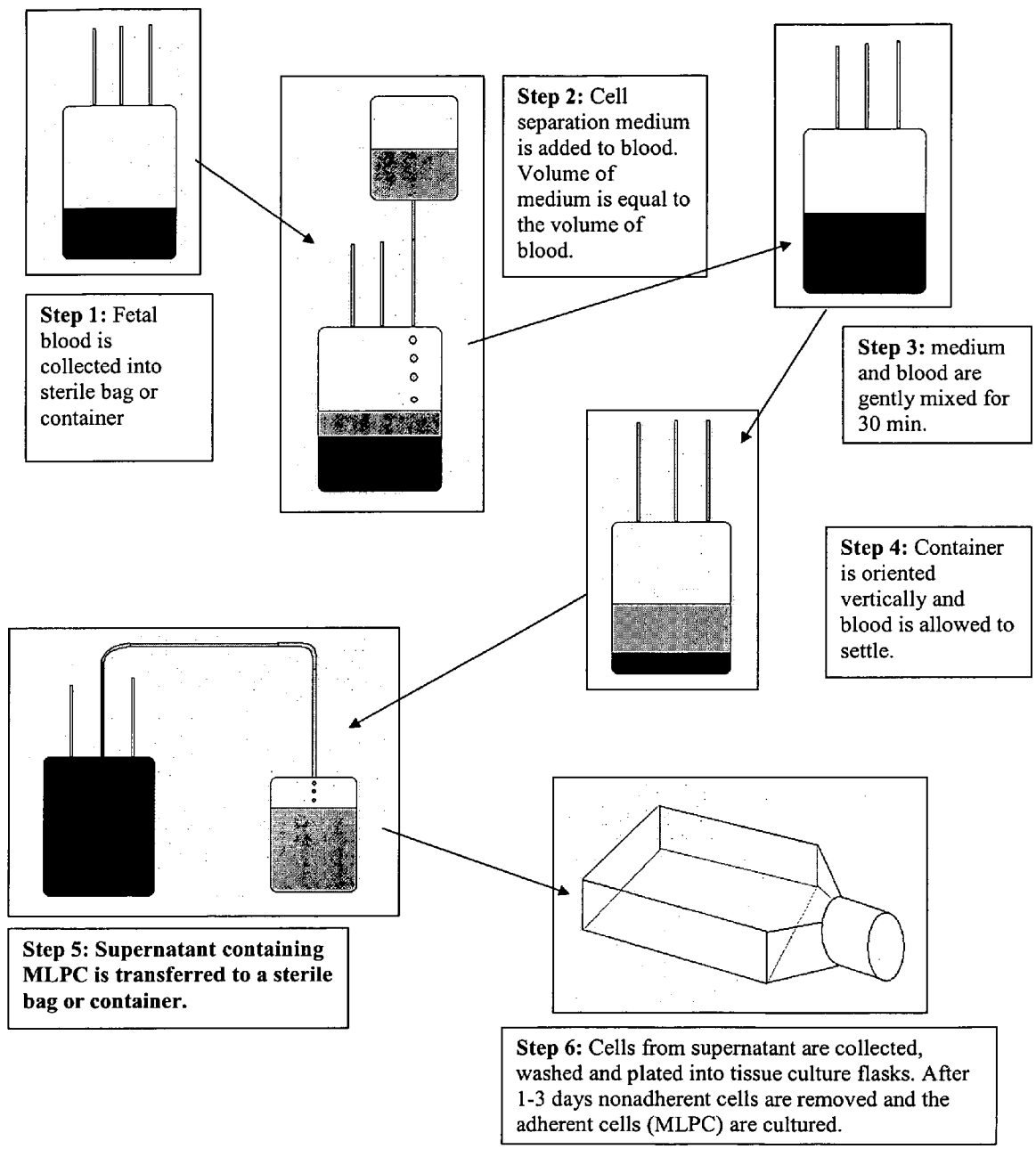
FIG. 1 is a schematic of a cell separation procedure for purifying MLPC from fetal blood.

In general, the invention provides purified populations of MLPC from human fetal blood (e.g., umbilical cord blood ("cord blood"), placental blood, or the blood from a fetus) and clonal MLPC lines derived from individual MLPC. Fetal blood provides a source of cells that is more immature than adult bone marrow and has a higher percentage of cells bearing immature cell surface markers. Consequently, there may be advantages in the expansion and differentiation capacity of the progenitor cells from fetal blood. As described herein, MLPC have immunophenotypic characteristics and a gene expression profile distinct from bone marrow derived MSC's, bone marrow-derived HSC, and umbilical cord blood-derived HSC and USSC. The cells described herein have the capacity to self renew and differentiate into diverse cells and tissue types. For example, MLPC are capable of differentiating to mature hepatocytes as shown below. MLPC can be used to develop cellular therapies and establish cryopreserved cell banks for future regenerative medicine procedures. MLPC also can be modified such that the cells can produce one or more polypeptides or other therapeutic compounds of interest.

Cell Separation Compositions

MLPC can be isolated from fetal blood (e.g., cord blood) using the negative selection process and cell separation compositions disclosed in U.S. Patent Publication No. 2003-0027233-A1. Such cell compositions can include dextran and one or more antibodies against (i.e., that have binding affinity for) a cell surface antigen.

Dextran is a polysaccharide consisting of glucose units linked predominantly in alpha (1 to 6) mode. Dextran can cause stacking of erythrocytes (i.e., rouleau formation) and thereby facilitate the removal of erythroid cells from solution. Antibodies against cell surface antigens can facilitate the removal of blood cells from solution via homotypic agglutination (i.e., agglutination of cells of the same cell type) and/or heterotypic agglutination (i.e., agglutination of cells of different cell types).

For example, a cell separation composition can include dextran and antibodies against glycophorin A, CD15, and CD9. Cell separation compositions also can contain antibodies against other blood cell surface antigens including, for example, CD2, CD3, CD4, CD8, CD72, CD16, CD41a, HLA Class I, HLA-DR, CD29, CD11a, CD11b, CD11c, CD19, CD20, CD23, CD39, CD40, CD43, CD44, CDw49d, CD53, CD54, CD62L, CD63, CD66, CD67, CD81, CD82, CD99, CD100, Leu-13, TPA-1, surface Ig, and combinations thereof. Thus, cell separation compositions can be formulated to selectively agglutinate particular types of blood cells.

Typically, the concentration of anti-glycophorin A antibodies in a cell separation composition ranges from 0.1 to 15 mg/L (e.g., 0.1 to 10 mg/L, 1 to 5 mg/L, or 1 mg/L). Anti-glycophorin A antibodies can facilitate the removal of red cells from solution by at least two mechanisms. First, anti-glycophorin A antibodies can cause homotypic agglutination of erythrocytes since glycophorin A is the major surface glycoprotein on erythrocytes. In addition, anti-glycophorin A antibodies also can stabilize dextran-mediated rouleau formation. Exemplary monoclonal anti-glycophorin A antibodies include, without limitation, 107FMN (Murine IgG1 isotype), YTH89.1 (Rat IgG2b isotype), 2.2.2.E7 (Murine IgM isotype; BioE, St. Paul, Minn.), and E4 (Murine IgM isotype). See e.g., M. Vanderlaan et al., *Molecular Immunology* 20:1353 (1983); Telen M. J. and Bolk, T. A., *Transfusion* 27: 309 (1987); and Outram S. et al., *Leukocyte Research.* 12:651 (1988).

The concentration of anti-CD15 antibodies in a cell separation composition can range from 0.1 to 15 mg/L (e.g., 0.1 to 10, 1 to 5, or 1 mg/L). Anti-CD15 antibodies can cause homotypic agglutination of granulocytes by crosslinking CD15 molecules that are present on the surface of granulocytes. Anti CD15 antibodies also can cause homotypic and heterotypic agglutination of granulocytes with monocytes, NK-cells and B-cells by stimulating expression of adhesion molecules (e.g., L-selectin and beta-2 integrin) on the surface of granulocytes that interact with adhesion molecules on monocytes, NK-cells and B-cells. Heterotypic agglutination of these cell types can facilitate the removal of these cells from solution along with red cell components. Exemplary monoclonal anti-CD15 antibodies include, without limitation, AHN1.1 (Murine IgM isotype), FMC-10 (Murine IgM isotype), BU-28 (Murine IgM isotype), MEM-157 (Murine IgM isotype), MEM-158 (Murine IgM isotype), 324.3.B9 (Murine IgM isotype; BioE, St. Paul, Minn.), and MEM-167 (Murine IgM isotype). See e.g., *Leukocyte typing IV* (1989); *Leukocyte typing II* (1984); *Leukocyte typing VI* (1995); Solter D. et al., *Proc. Natl. Acad. Sci. USA* 75:5565 (1978); Kannagi R. et al., *J. Biol. Chem.* 257:14865 (1982); Magnani, J. L. et al., *Arch. Biochem. Biophys* 233:501 (1984); Eggens I. et al., *J. Biol. Chem.* 264:9476 (1989).

The concentration of anti-CD9 antibodies in a cell separation composition can range from 0.1 to 15, 0.1 to 10, 1 to 5, or 1 mg/L. Anti-CD9 antibodies can cause homotypic agglutination of platelets. Anti-CD9 antibodies also can cause heterotypic agglutination of granulocytes and monocytes via platelets that have adhered to the surface of granulocytes and monocytes. CD9 antibodies can promote the expression of platelet p-selectin (CD62P), CD41/61, CD31, and CD36, which facilitates the binding of platelets to leukocyte cell surfaces. Thus, anti-CD9 antibodies can promote multiple cell-cell linkages and thereby facilitate agglutination and removal from solution. Exemplary monoclonal anti-CD9 antibodies include, without limitation, MEM-61 (Murine IgG1 isotype), MEM-62 (Murine IgG1 isotype), MEM-192 (Murine IgM isotype), FMC-8 (Murine IgG2a isotype), SN4 (Murine IgG1 isotype), 8.10.E7 (Murine IgM isotype; BioE, St. Paul, Minn.), and BU-16 (Murine IgG2a isotype). See e.g., *Leukocyte typing VI* (1995); *Leukocyte typing II* (1984); Von dem Bourne A. E. G. Kr. and Moderman P. N. (1989) In *Leukocyte typing IV* (ed. W. Knapp, et al), pp. 989-92, Oxford University Press, Oxford; Jennings, L. K., et al. *In Leukocyte typing V*, ed. S. F. Schlossmann et al., pp. 1249-51, Oxford University Press, Oxford (1995); Lanza F. et al., *J. Biol. Chem.* 266:10638 (1991); Wright et al., *Immunology Today* 15:588 (1994); Rubinstein E. et al., *Seminars in Thrombosis and Hemostasis* 21:10 (1995).

In some embodiments, a cell separation composition contains antibodies against CD41, which can selectively agglutinate platelets. In some embodiments, a cell separation composition contains antibodies against CD3, which can selectively agglutinate T-cells. In some embodiments, a cell separation composition contains antibodies against CD2, which can selectively agglutinate T-cells and NK cells. In some embodiments, a cell separation composition contains antibodies against CD72, which can selectively agglutinate B-cells. In some embodiments, a cell separation composition contains antibodies against CD16, which can selectively agglutinate NK cells and neutrophilic granulocytes. The concentration of each of these antibodies can range from 0.01 to 15 mg/L. Exemplary anti-CD41 antibodies include, without limitation, PLT-1 (Murine IgM isotype), CN19 (Murine $IgG_1$ isotype), and 8.7.C3 (Murine IgG1 isotype). Non-limiting examples of anti-CD3 antibodies include OKT3 (Murine $IgG_1$), HIT3a (Murine IgG2a isotype), SK7 (Murine $IgG_1$) and BC3 (Murine $IgG_{2a}$). Non-limiting examples of anti-CD2 antibodies include 7A9 (Murine IgM isotype), T11 (Murine $IgG_1$ isotype), and Leu5b (Murine $IgG_{2a}$ Isotype). Non-limiting examples of anti-CD72 antibodies include BU-40 (Murine $IgG_1$ isotype) and BU-41 (Murine $IgG_1$ isotype). Non-limiting examples of anti-CD16 antibodies include 3G8 (Murine IgG).

As mentioned above, cell separation compositions can be formulated to selectively agglutinate particular blood cells. As an example, a cell separation composition containing antibodies against glycophorin A, CD15, and CD9 can facilitate the agglutination of erythrocytes, granulocytes, NK cells, B cells, and platelets. T cells, NK cells and rare precursor cells such as MLPC then can be recovered from solution. If the formulation also contained an antibody against CD3, T cells also could be agglutinated, and NK cells and rare precursors such as MLPC could be recovered from solution.

Cell separation compositions can contain antibodies against surface antigens of other types of cells (e.g., cell surface proteins of tumor cells). Those of skill in the art can use routine methods to prepare antibodies against cell surface antigens of blood, and other, cells from humans and other mammals, including, for example, non-human primates, rodents (e.g., mice, rats, hamsters, rabbits and guinea pigs), swine, bovines, and equines.

Typically, antibodies used in the composition are monoclonal antibodies, which are homogeneous populations of antibodies to a particular epitope contained within an antigen. Suitable monoclonal antibodies are commercially available, or can be prepared using standard hybridoma technology. In particular, monoclonal antibodies can be obtained by techniques that provide for the production of antibody molecules by continuous cell lines in culture, including the technique described by Kohler, G. et al., *Nature,* 1975, 256:495, the human B-cell hybridoma technique (Kosbor et al., *Immunology Today* 4:72 (1983); Cole et al., *Proc. Natl. Acad. Sci. USA* 80:2026 (1983)), and the EBV-hybridoma technique (Cole et al., "Monoclonal Antibodies and Cancer Therapy," Alan R. Liss, Inc., pp. 77-96 (1983)).

Antibodies can be of any immunoglobulin class including IgG, IgM, IgE, IgA, IgD, and any subclass thereof. Antibodies of the IgG and IgM isotypes are particularly useful in cell separation compositions of the invention. Pentameric IgM antibodies contain more antigen binding sites than IgG antibodies and can, in some cases (e.g., anti-glycophorin A and anti-CD15), be particularly useful for cell separation reagents. In other cases (e.g., anti-CD9 antibodies), antibodies of the IgG isotype are particularly useful for stimulating homotypic and/or heterotypic agglutination.

Antibodies against cell surface antigens can be provided in liquid phase (i.e., soluble). Liquid phase antibodies typically are provided in a cell separation composition at a concentration between about 0.1 and about 15 mg/l (e.g., between 0.25 to 10, 0.25 to 1, 0.5 to 2, 1 to 2, 4 to 8, 5 to 10 mg/l).

Antibodies against cell surface antigens also can be provided in association with a solid phase (i.e., substrate-bound). Antibodies against different cell surface antigens can be covalently linked to a solid phase to promote crosslinking of cell surface molecules and activation of cell surface adhesion molecules. The use of substrate-bound antibodies can facilitate cell separation (e.g., by virtue of the mass that the particles contribute to agglutinated cells, or by virtue of properties useful for purification).

In some embodiments, the solid phase with which a substrate-bound antibody is associated is particulate. In some embodiments, an antibody is bound to a latex microparticle such as a paramagnetic bead (e.g., via biotin-avidin linkage, covalent linkage to COO groups on polystyrene beads, or covalent linkage to $NH_2$ groups on modified beads). In some embodiments, an antibody is bound to an acid-etched glass particle (e.g., via biotin-avidin linkage). In some embodiments, an antibody is bound to an aggregated polypeptide such as aggregated bovine serum albumin (e.g., via biotin-avidin linkage, or covalent linkage to polypeptide COO groups or $NH_2$ groups). In some embodiments, an antibody is covalently linked to a polysaccharide such as high molecular weight (e.g., >1,000,000 $M_r$) dextran sulfate. In some embodiments, biotinylated antibodies are linked to avidin particles, creating tetrameric complexes having four antibody molecules per avidin molecule. In some embodiments, antibodies are bound to biotinylated agarose gel particles (One Cell Systems, Cambridge, Mass., U.S.A.) via biotin-avidin-biotinylated antibody linkages. Such particles typically are about 300-500 microns in size, and can be created in a sonicating water bath or in a rapidly mixed water bath.

Cell-substrate particles (i.e., particles including cells and substrate-bound antibodies) can sediment from solution as an agglutinate. Cell-substrate particles also can be removed from solution by, for example, an applied magnetic field, as when the particle is a paramagnetic bead. Substrate-bound antibodies typically are provided in a cell separation composition at a concentration between about 0.1 and about $50.0 \times 10^9$ particles/l (e.g., between 0.25 to $10.0 \times 10^9$, 1 to $20.0 \times 10^9$, 2 to $10.0 \times 10^9$, 0.5 to $2 \times 10^9$, 2 to $5 \times 10^9$, 5 to $10 \times 10^9$, and 10 to $30 \times 10^9$ particles/l), where particles refers to solid phase particles having antibodies bound thereto.

Cell separation compositions also can contain divalent cations (e.g., $Ca^{+2}$ and $Mg^{+2}$). Divalent cations can be provided, for example, by a balanced salt solution (e.g., Hank's balanced salt solution). $Ca^{+2}$ ions reportedly are important for selectin-mediated and integrin-mediated cell-cell adherence.

Cell separation compositions also can contain an anticoagulant such as heparin. Heparin can prevent clotting and non-specific cell loss associated with clotting in a high calcium environment. Heparin also promotes platelet clumping. Clumped platelets can adhere to granulocytes and monocytes and thereby enhance heterotypic agglutination more so than single platelets. Heparin can be supplied as a heparin salt (e.g., sodium heparin, lithium heparin, or potassium heparin).

Populations and Clonal Lines of MLPC

MLPC can be purified from human fetal blood using a cell separation composition described above. As used herein, "purified" means that at least 90% (e.g., 91, 92, 93, 94, 95, 96, 97, 98, or 99%) of the cells within the population are MLPC. As used herein, "MLPC" refers to fetal blood cells that are positive for CD9 and typically display a constellation of other markers such as CD13, CD73, and CD105. "MLPC population" refers to the primary culture obtained from the human fetal blood and uncloned progeny thereof. "Clonal line" refers to a cell line derived from a single cell. As used herein, a "cell line" is a population of cells able to renew themselves for extended periods of times in vitro under appropriate culture conditions. The term "line," however, does not indicate that the cells can be propagated indefinitely. Rather, clonal lines described herein typically can undergo 75 to 100 doublings before senescing.

Typically, an MLPC population is obtained by contacting a fetal blood sample with a cell separation composition described above and allowing the sample to partition into an agglutinate and a supernatant phase. For example, the sample can be allowed to settle by gravity or by centrifugation. Preferably, MLPC are purified from an umbilical cord blood sample that is less than 48 hours old (e.g., less than 24, 12, 8, or 4 hours post-partum). After agglutination, unagglutinated cells can be recovered from the supernatant phase. For example, cells in the supernatant phase can be recovered by centrifugation then washed with a saline solution and plated on a solid substrate (e.g., a plastic culture device such as a chambered slide or culture flask), using a standard growth medium with 10% serum (e.g., DMEM with 10% serum; RPMI-1640 with 10% serum, or mesenchymal stem cell growth medium with 10% serum (catalog # PT-3001, Cambrex, Walkersville, Md.). MLPC attach to the surface of the solid substrate while other cells, including T cells, NK cells and CD34$^+$ HSC, do not and can be removed with washing. The MLPC change from the leukocyte morphology to the fibroblastic morphology between 3 days and 2 weeks post initiation of culture after which the cells enter logarithmic growth phase and will continue growing logarithmically as long as cultures are maintained at cell concentrations of less than about $1.5 \times 10^5$ cells/cm$^2$.

Clonal lines can be established by harvesting the MLPC then diluting and re-plating the cells on a multi-well culture plate such that a single cell can be found in a well. Cells can be transferred to a larger culture flask after a concentration of 1 to $5 \times 10^5$ cells/75 cm$^2$ is reached. Cells can be maintained at a concentration between $1 \times 10^5$ and $5 \times 10^5$ cells/75 cm$^2$ for logarithmic growth. See, e.g., U.S. Patent Publication No. 2005-0255592-A.

MLPC can be assessed for viability, proliferation potential, and longevity using techniques known in the art. For example, viability can be assessed using trypan blue exclusion assays, fluorescein diacetate uptake assays, or propidium iodide uptake assays. Proliferation can be assessed using thymidine uptake assays or MTT cell proliferation assays. Longevity can be assessed by determining the maximum number of population doublings of an extended culture.

MLPC can be immunophenotypically characterized using known techniques. For example, the cell culture medium can be removed from the tissue culture device and the adherent cells washed with a balanced salt solution (e.g., Hank's balanced salt solution) and bovine serum albumin (e.g., 2% BSA). Cells can be incubated with an antibody having binding affinity for a cell surface antigen such as CD9, CD45, CD13, C73, CD105, or any other cell surface antigen. The antibody can be detectably labeled (e.g., fluorescently or enzymatically) or can be detected using a secondary antibody that is detectably labeled. Alternatively, the cell surface antigens on MLPC can be characterized using flow cytometry and fluorescently labeled antibodies.

As described herein, the cell surface antigens present on MLPC can vary, depending on the stage of culture. Early in culture when MLPC display a leukocyte-like morphology, MLPC are positive for CD9 and CD45, SSEA-4 (stage-specific embryonic antigen-4), CD34, as well as CD13, CD29, CD44, CD73, CD90, CD105, stem cell factor, STRO-1 (a cell surface antigen expressed by bone marrow stromal cells), SSEA-3(galactosylgloboside), and CD133, and are negative for CD15, CD38, glycophorin A (CD235a), and lineage markers CD2, CD3, CD4, CD5, CD7, CD8, CD10, CD11b, CD16, CD19, CD20, CD21, CD22, CD33, CD36, CD41, CD61, CD62E, CD72, HLA-DR, and CD102. After transition to the fibroblastic morphology, MLPC remain positive for CD9, CD13, CD29, CD44, CD73, CD90, and CD105, and become negative for CD34, CD41, CD45, stem cell factor, STRO-1, SSEA-3, SSEA-4, and CD133. At all times during in vitro culture, the undifferentiated MLPC are negative for CD15, CD38, glycophorin A (CD235a), and lineage markers CD2, CD3, CD4, CD5, CD7, CD8, CD10, CD11b, CD16, CD 19, CD20, CD21, CD22, CD33, CD36, CD41, CD61, CD62E, CD72, HLA-DR, and CD102.

Bone marrow-derived MSC and MAPC as well as the cord blood-derived USSC have been described as being derived from a CD45$^-$/CD34$^-$ cell population. MLPC are distinguished from those cell types as being a CD45$^+$/CD34$^+$ derived cell. Additionally, the presence and persistence of CD9 on the fetal blood-derived MLPC at all stages of maturation further distinguishes MLPC from MSC and MAPC, which do not possess CD9 as a marker. CD9 is expressed as a marker on human embryonic stem cells. MLPC, which share the hematopoietic markers CD45, CD133, CD90 and CD34 during their leukocyte morphology phase, can be distinguished from HSC by their obligate plastic adherence and the presence of mesenchymal associated markers CD105, CD29, CD73, CD13 and embryonic associated markers SSEA-3 and SSEA-4. Additionally using currently available technology, HSC are unable to be cultured in vitro without further differentiation while MLPC can be expanded for many generations without differentiation. MLPC also differ from MSC and USSC by their more gracile in vitro culture appearance, thread-like cytoplasmic projections and their preference for low density culture conditions for optimal growth.

MLPC also can be characterized based on the expression of one or more genes. Methods for detecting gene expression can include, for example, measuring levels of the mRNA or protein of interest (e.g., by Northern blotting, reverse-transcriptase (RT)-PCR, microarray analysis, Western blotting, ELISA, or immunohistochemical staining). The gene expression profile of MLPC is significantly different than other cell types. Microarray analysis indicated that the MLPC lines have an immature phenotype that differs from the phenotypes of, for example, CD133+HSC, lineage negative cells (Forrz et al., *Stem Cells*, 22(1):100-108 (2004)), and MSC (catalog #PT-2501, Cambrex, Walkersville, Md., U.S. Pat. No. 5,486,359), which demonstrate a significant degree of commitment down several lineage pathways. See, e.g., U.S. Patent Publication No. 2006-0040392-A1.

Comparison of the gene expression profile of MLPC and MSC demonstrates MSC are more committed to connective tissue pathways. There are 80 genes up-regulated in MSC, and 152 genes up-regulated in MLPC. In particular, the following genes were up-regulated in MLPC when compared with MSC, i.e., expression was decreased in MSC relative to MLPC: ITGB2, ARHGAP9, CXCR4, INTEGRINB7, PECAM1, PRKCB_1, PRKCB_3, IL7R, AIF1, CD45_EX10-11, PLCG2, CD37, PRKCB_2, TCF2_1, RNF138, EAAT4, EPHA1, RPLP0, PTTG, SERPINA1_2, ITGAX, CD24, F11R, RPL4, ICAM1, LMO2, HMGB2, CD38, RPL7A, BMP3, PTHR2, S100B, OSF, SNCA, GRIK1, HTR4, CHRM1, CDKN2D, HNRPA1, IL6R, MUSLAMR, ICAM2, CSK, ITGA6, MMP9, DNMT1, PAK1, IKKB, TFRC_MIDDLE, CHI3L2, ITGA4, FGF20, NBR2, TNFRSF1B, CEBPA_3, CDO1, NFKB1, GATA2, PDGFRB, ICSBP1, KCNE3, TNNC1, ITGA2B, CCT8, LEFTA, TH, RPS24, HTR1F, TREM1, CCNB2, SELL, CD34, HMGIY, COX7A2, SELE, TNNT2, SEM2, CHEK1, CLCN5, F5, PRKCQ, ITGAL, NCAM2, ZNF257-MGC12518-ZNF92-ZNF43-ZNF273-FLJ90430, CDK1, RPL6, RPL24, IGHA1-IGHA2_M, PUM2, GJA7, HTR7, PTHR1, MAPK14, MSI2_1, KCNJ3, CD133, SYP, TFRC_5PRIME, TDGF1-TDGF3_2, FLT3, HPRT, SEMA4D, ITGAM, KIAA0152_3, ZFP42, SOX20, FLJ21190, CPN2, POU2F2, CASP8_1, CLDN10, TREM2, TERT, OLIG1, EGR2, CD44_EX3-5, CD33, CNTFR, OPN, COL9A1_2, ROBO4, HTR1D_1, IKKA, KIT, NPPA, PRKCH, FGF4, CD68, NUMB, NRG3, SALL2, NOP5, HNF4G, FIBROMODULIN, CD58, CALB1, GJB5, GJA5, POU5F_1, GDF5, POU6F1, CD44_EX16-20, BCAN, PTEN1-PTEN2, AGRIN, ALB, KCNQ4, DPPA5, EPHB2, TGFBR2, and ITGA3. See, e.g., U.S. Patent Publication No. 2006-0040392-A1.

MLPC express a number of genes associated with "stemness," which refers to the ability to self-renew undifferentiated and ability to differentiate into a number of different cell types. Genes associated with "stemness" include the genes known to be over-expressed in human embryonic stem cells, including, for example, POU5F (Oct4), TERT, and ZFP42. For example, 65 genes associated with protein synthesis are down-regulated, 18 genes linked with phosphate metabolism are down-regulated, 123 genes regulating proliferation and cell cycling are down-regulated, 12 different gene clusters associated with differentiation surface markers are down-regulated, e.g., genes associated with connective tissue, including integrin alpha-F, laminin and collagen receptor, ASPIC, thrombospondins, endothelium endothelin-1 and -2 precursors, epidermal CRABP-2, and genes associated with adipocytes, including, for example, the leptin receptor, and 80 genes linked to nucleic acid binding and regulation of differentiation are up-regulated. Thus, the immaturity of a population of MLPC can be characterized based on the expression of one or more genes (e.g., one or more of CXCR4, FLT3, TERT, KIT, POU5F, or hematopoietic CD markers such as CD9, CD34, and CD133). See, e.g., U.S. Patent Publication No. 2006-0040392-A1.

MLPC can be cryopreserved by suspending the cells (e.g. $5 \times 10^6$ to $2 \times 10^7$ cells/mL) in a cryopreservative such as dimethylsulfoxide (DMSO, typically 1 to 10%) or in fetal bovine serum, human serum, or human serum albumin in combination with one or more of DMSO, trehalose, and dextran. For example, (1) fetal bovine serum containing 10% DMSO; (2) human serum containing 10% DMSO and 1% Dextran; (3) human serum containing 1% DMSO and 5% trehalose; or (4) 20% human serum albumin, 1% DMSO, and 5% trehalose can be used to cryopreserve MLPC. After adding cryopreservative, the cells can be frozen (e.g., to −90° C.). In some embodiments, the cells are frozen at a controlled rate (e.g., controlled electronically or by suspending the cells in a bath of 70% ethanol and placed in the vapor phase of a liquid nitrogen storage tank. When the cells are chilled to −90° C., they can be placed in the liquid phase of the liquid nitrogen storage tank for long term storage. Cryopreservation can allow for long-term storage of these cells for therapeutic use.

Differentiation of MLPC

MLPC are capable of differentiating into a variety of cells, including cells of each of the three embryonic germ layers (i.e., endoderm, ectoderm, and mesoderm). As used herein, "capable of differentiating" means that a given cell, or its progeny, can proceed to a differentiated phenotype under the appropriate culture conditions. For example, MLPC can differentiate into cells having an osteocytic phenotype, cells having an adipocytic phenotype, cells having a neurocytic phenotype, cells having a myocytic phenotype, cells having an endothelial phenotype, cells having a hepatocytic/pancreatic precursor phenotype (also known as an oval cell), cells having a mature hepatocyte phenotype, as well as other cell types. A clonal population of differentiated cells (e.g., mature hepatocytes) is obtained when a clonal line of MLPC is differentiated.

Differentiation can be induced using one or more differentiation agents, including without limitation, $Ca^{2+}$, an epidermal growth factor (EGF), a platelet derived growth factor (PDGF), a keratinocyte growth factor (KGF), a transforming growth factor (TGF), cytokines such as an interleukin, an interferon, or tumor necrosis factor, retinoic acid, transferrin, hormones (e.g., androgen, estrogen, insulin, prolactin, triiodothyronine, hydrocortisone, or dexamethasone), sodium butyrate, TPA, DMSO, NMF (N-methyl formamide), DMF (dimethylformamide), or matrix elements such as collagen, laminin, heparan sulfate).

Determination that an MLPC has differentiated into a particular cell type can be assessed using known methods, including, measuring changes in morphology and cell surface markers (e.g., by flow cytometry or immunohistochemistry), examining morphology by light or confocal microscopy, or by measuring changes in gene expression using techniques such as polymerase chain reaction (PCR) or gene-expression profiling.

For example, MLPC can be induced to differentiate into cells having an osteocytic phenotype using an induction medium (e.g., Osteogenic Differentiation Medium, catalog # PT-3002, from Cambrex) containing dexamethasone, L-glutamine, ascorbate, and β-glycerophosphate (Jaiswal et al., *J. Biol. Chem.* 64(2):295-312 (1997)). Cells having an osteocytic phenotype contain deposits of calcium crystals, which can be visualized, for example, using Alizarin red stain.

MLPC can be induced to differentiate into cells having an adipocytic phenotype using an induction medium (e.g., Adipogenic Differentiation Medium, catalog # PT-3004, from Cambrex) containing insulin, L-glutamine, dexamethasone, indomethacin, and 3-isobutyl-1-methyl-xanthine. Cells having an adipocytic phenotype contain lipid filled liposomes that can be visualized with Oil Red stain. Such cells also contain trigycerides, which fluoresce green with Nile Red stain (Fowler and Greenspan, *Histochem. Cytochem.* 33:833-836 (1985)).

MLPC can be induced to differentiate into cells having a myocytic phenotype using an induction medium (e.g., SkGM™, catalog # CC-3160, from Cambrex) containing EGF, insulin, Fetuin, dexamethasone, and FGF-basic (Wernet, et al., U.S. patent publication 20020164794 A1). Cells having a myocytic phenotype express fast skeletal muscle myosin and alpha actinin.

MLPC can be induced to differentiate into cells having a neural stem cell phenotype (neurospheres) using an induction medium (e.g., NPMM™—Neural Progenitor Maintenance medium, catalog #CC-3209, from Cambrex) containing human FGF-basic, human EGF, NSF-1, and FGF-4 and a culture device pre-coated with poly-D-lysine and laminin (e.g., from BD Biosciences Discovery Labware, catalog #354688). Once cells have been differentiated into neurospheres, they can be further differentiated into motor neurons with the addition of brain-derived neurotrophic factor (BDNF) and neurotrophin-3 (NT-3), astrocytes with the addition of leukemia inhibitory factor (LIF), retinoic acid and ciliary neurotrophic factor, and oligodendrocytes with the addition of 3,3',5-triiodo-L-thyronine (T3). Neurocytic differentiation can be confirmed by the expression of nestin, class III beta-tubulin (tubulin β-4), glial fibrillary acidic protein (GFAP), and galactocerebroside (GalC). Neurospheres are positive for all such markers while some differentiated cell types are not. Differentiation into oligodendrocytes can be confirmed by positive staining for myelin basic protein (MBP).

MLPC can be induced to differentiate into cells having an endothelial phenotype using an endothelial growth medium (e.g., EGM™-MV, catalog # CC-3125, from Cambrex) containing heparin, bovine brain extract, epithelial growth factor (e.g., human recombinant epithelial growth factor), and hydrocortisone. Endothelial differentiation can be confirmed by expression of E-selectin (CD62E), ICAM-2 (CD102), CD34, and STRO-1.

MLPC can be induced to differentiate into cells having a hepatocyte/pancreatic precursor cell phenotype using a differentiation medium (e.g., HCM™—hepatocyte culture medium, catalog # CC-3198, from Cambrex) containing ascorbic acid, hydrocortisone, transferrin, insulin, EGF (e.g., human EGF), hepatocyte growth factor (e.g., recombinant human hepatocyte growth factor), fibroblast growth factor-basic (e.g., human FGF-basic), fibroblast growth factor-4 (e.g., recombinant human FGF-4), and stem cell factor. Liver and pancreas cells share a common progenitor. Hepatocyte differentiation can be confirmed by expression of hepatocyte growth factor receptor and human serum albumin. Pancreatic cell differentiation can be confirmed by production of insulin and pro-insulin.

MLPC can be induced to differentiate into mature hepatocytes by culturing MLPC in a three-dimensional scaffold in the presence of a differentiation medium (e.g., HCM™) as discussed above. The three-dimensional scaffold can act as a framework that supports the growth of the cells in multiple layers. In some embodiments, the scaffold can be composed of collagen (e.g., a mixture of collagens from bovine hide or rat tails). Such scaffolds are biodegradable. In other embodiments, collagen or other extracellular matrix protein is coated on a scaffold composed of one or more materials such as polyamides; polyesters; polystyrene; polypropylene; polyacrylates; polyvinyl compounds; polycarbonate; polytetrafluoroethylene (PTFE, Teflon); thermanox; nitrocellulose; poly (α-hydroxy acids) such as polylactic acid (PLA), polyglycolic acid (PGA), poly(ortho esters), polyurethane, calcium phosphate, and hydrogels such as polyhydroxyethylmethacrylate or polyethylene oxide/polypropylene oxide copolymers); hyaluronic acid, cellulose; and dextran. See, for example, U.S. Pat. No. 5,624,840. PLA, PGA, and hyaluronic acid are biodegradable. Suitable three-dimensional scaffolds are commercially available. For example, the BD™ three-dimensional collagen composite scaffold from BD Sciences (San Jose, Calif.), hyaluronan scaffold from Lifecore Biomedical (Chaska, Minn.), alginate scaffold from NovaMatrix (Philadelphia, Pa.), or the calcium phosphate scaffold from Phillips Plastic (Prescott, Wis.) can be used.

Differentiation into mature hepatocytes can be confirmed by the presence of hepatocyte growth factor receptor and intracellular human serum albumin and the absence of intracellular pancreas-associated insulin or proinsulin production. Hepatocyte function can be confirmed by production of hepatocyte-specific proteins (e.g., alpha fetoprotein) and enzymatic activity (e.g., cytochrome P450). Clonal populations of mature hepatocytes (i.e., a plurality of mature hepatocytes obtained from a clonal line of MLPC) are particularly useful, for example, in liver assist devices, for producing biologically active molecules in bioreactors, transplantation or implantation in vivo, and analyzing toxicity of drugs or other compounds in vitro. Toxicity assays (e.g., measurement of ATP content or leakage of lactate dehydrogenase) performed with such clonal populations are consistent over time as the same genotype can be used repeatedly.

Populations of mature hepatocytes (e.g., clonal populations) housed within a three-dimensional scaffold can be cryopreserved as discussed above for MLPC. For example, a three-dimensional scaffold housing a clonal population of mature hepatocytes can be cryopreserved using 10% DMSO in fetal bovine serum in liquid nitrogen.

Modified Populations of MLPC

MLPC can be modified such that the cells can produce one or more polypeptides or other therapeutic compounds of interest. To modify the isolated cells such that a polypeptide or other therapeutic compound of interest is produced, the appropriate exogenous nucleic acid must be delivered to the cells. In some embodiments, the cells are transiently transfected, which indicates that the exogenous nucleic acid is episomal (i.e., not integrated into the chromosomal DNA). In other embodiments, the cells are stably transfected, i.e., the exogenous nucleic acid is integrated into the host cell's chromosomal DNA. The term "exogenous" as used herein with reference to a nucleic acid and a particular cell refers to any nucleic acid that does not originate from that particular cell as found in nature. In addition, the term "exogenous" includes a naturally occurring nucleic acid. For example, a nucleic acid encoding a polypeptide that is isolated from a human cell is an exogenous nucleic acid with respect to a second human cell once that nucleic acid is introduced into the second human cell. The exogenous nucleic acid that is delivered typically is part of a vector in which a regulatory element such as a promoter is operably linked to the nucleic acid of interest.

Cells can be engineered using a viral vector such as an adenovirus, adeno-associated virus (AAV), retrovirus, lentivirus, vaccinia virus, measles viruses, herpes viruses, or bovine papilloma virus vector. See, Kay et al. (1997) *Proc. Natl. Acad. Sci. USA* 94:12744-12746 for a review of viral and non-viral vectors. A vector also can be introduced using mechanical means such as liposomal or chemical mediated uptake of the DNA. For example, a vector can be introduced into an MLPC by methods known in the art, including, for example, transfection, transformation, transduction, electroporation, infection, microinjection, cell fusion, DEAE dextran, calcium phosphate precipitation, liposomes, LIPOFECTIN™, lysosome fusion, synthetic cationic lipids, use of a gene gun or a DNA vector transporter.

A vector can include a nucleic acid that encodes a selectable marker. Non-limiting examples of selectable markers include puromycin, adenosine deaminase (ADA), aminoglycoside phosphotransferase (neo, G418, APH), dihydrofolate reductase (DHFR), hygromycin-B-phosphtransferase, thymidine kinase (TK), and xanthin-guanine phosphoribosyltransferase (XGPRT). Such markers are useful for selecting stable transformants in culture.

MLPC also can have a targeted gene modification. Homologous recombination methods for introducing targeted gene modifications are known in the art. To create a homologous recombinant MLPC, a homologous recombination vector can be prepared in which a gene of interest is flanked at its 5' and 3' ends by gene sequences that are endogenous to the genome of the targeted cell, to allow for homologous recombination to occur between the gene of interest carried by the vector and the endogenous gene in the genome of the targeted cell. The additional flanking nucleic acid sequences are of sufficient length for successful homologous recombination with the endogenous gene in the genome of the targeted cell. Typically, several kilobases of flanking DNA (both at the 5' and 3' ends) are included in the vector. Methods for constructing homologous recombination vectors and homologous recombinant animals from recombinant stem cells are commonly known in the art (see, e.g., Thomas and Capecchi, 1987, *Cell* 51:503; Bradley, 1991, *Curr. Opin. Bio/Technol.* 2:823-29; and PCT Publication Nos. WO 90/11354, WO 91/01140, and WO 93/04169.

Methods of Using MLPC

The MLPC can be used in enzyme replacement therapy to treat specific diseases or conditions, including, but not limited to lysosomal storage diseases, such as Tay-Sachs, Niemann-Pick, Fabry's, Gaucher's, Hunter's, and Hurler's syndromes, as well as other gangliosidoses, mucopolysaccharidoses, and glycogenoses.

In other embodiments, the cells can be used as carriers in gene therapy to correct inborn errors of metabolism, adrenoleukodystrophy, cystic fibrosis, glycogen storage disease, hypothyroidism, sickle cell anemia, Pearson syndrome, Pompe's disease, phenylketonuria (PKIJ), porphyrias, maple syrup urine disease, homocystinuria, mucoplysaccharidenosis, chronic granulomatous disease and tyrosinemia and Tay-Sachs disease or to treat cancer, tumors or other pathological conditions.

MLPC can be used to repair damage of tissues and organs resulting from disease. In such an embodiment, a patient can be administered a population of MLPC to regenerate or restore tissues or organs which have been damaged as a consequence of disease. For example, a population of MLPC can be administered to a patient to enhance the immune system following chemotherapy or radiation, to repair heart tissue following myocardial infarction, or to repair lung tissue after lung injury or disease.

The cells also can be used in tissue regeneration or replacement therapies or protocols, including, but not limited to treatment of corneal epithelial defects, cartilage repair, facial dermabrasion, mucosal membranes, tympanic membranes, intestinal linings, neurological structures (e.g., retina, auditory neurons in basilar membrane, olfactory neurons in olfactory epithelium), burn and wound repair for traumatic injuries of the skin, or for reconstruction of other damaged or diseased organs or tissues.

MLPC also can be used in therapeutic transplantation protocols, e.g., to augment or replace stem or progenitor cells of the liver, pancreas, kidney, lung, nervous system, muscular system, bone, bone marrow, thymus, spleen, mucosal tissue, gonads, or hair.

Compositions and Articles of Manufacture

The invention also features compositions and articles of manufacture containing purified populations of MLPC or clonal lines of MLPC. In some embodiments, the purified population of MLPC or clonal line is housed within a container (e.g., a vial or bag). In some embodiments, the clonal lines have undergone at least 3 doublings in culture (e.g., at least 4, 5, 6, 7, 8, 9, 10, 15, 20, 25, 30, 35, 40, 45, or 50 doublings). In other embodiments, a culture medium (e.g., MSCGM™ medium or HCM™) is included in the composition or article of manufacture. In still other embodiments, the composition or article of manufacture can include one or more cryopreservatives or pharmaceutically acceptable carriers. For example, a composition can include serum and DMSO, a mixture of serum, DMSO, and trehalose, or a mixture of human serum albumin, DMSO, and trehalose. Other components, such as a three-dimensional scaffold, also can be included in a composition or article of manufacture.

Purified populations of MLPC or clonal MLPC lines can be combined with packaging material and sold as a kit. For example, a kit can include purified populations of MLPC or clone MLPC lines, a differentiation medium effective to induce differentiation of the MLPC into cells having a mature hepatocyte phenotype, and a three-dimensional scaffold. The differentiation medium can include ascorbic acid, hydrocortisone, transferrin, insulin, EGF, hepatocyte growth factor, FGF-basic, fibroblast growth factor-4, and stem cell factor. The packaging material included in a kit typically contains instructions or a label describing how the purified populations of MLPC or clonal lines can be grown, differentiated, or used. A label also can indicate that the MLPC have enhanced expression of, for example, CXCR4, FLT3, or CD133 relative to a population of MSC. Components and methods for producing such kits are well known.

In other embodiments, an article of manufacture or kit can include differentiated progeny of MLPC or differentiated progeny of clonal MLPC lines. For example, an article of manufacture or kit can include a clonal population of mature hepatocytes and a culture medium, and further can include one or more cryopreservatives. In some embodiments, the clonal population of mature hepatocytes is housed within a three-dimensional scaffold or a container such as a vial or bag. The three-dimensional scaffold or container also can include one or more cryopreservatives. In still other embodiments, the three-dimensional scaffold housing the clonal population of mature hepatocytes is itself housed within a well of a multi-well culture plate. For example, an article of manufacture or kit can include a multi-well plate (e.g., a 48, 96, or 384 well plate) in which each well contains a three-dimensional scaffold housing a clonal population of mature hepatocytes.

An article of manufacture or kit also can include one or more reagents for characterizing a population of MLPC, a clonal MLPC line, or differentiated progeny of MLPC. For example, a reagent can be a nucleic acid probe or primer for detecting expression of a gene such as CXCR4, FLT3, CD133, CD34, TERT, KIT, POU5F, ICAM2, ITGAX, TFRC, KIT, IL6R, IL7R, ITGAM, FLT3, PDGFRB, SELE, SELL, TFRC, ITGAL, ITGB2, PECAM1, ITGA2B, ITGA3, ITGA4, ITGA6, ICAM1, CD24, CD44, CD45, CD58, CD68, CD33, CD37, or CD38. Such a nucleic acid probe or primer can be labeled, (e.g., fluorescently or with a radioisotope) to facilitate detection. A reagent also can be an antibody having specific binding affinity for a cell surface marker such as CD9, CD45, SSEA-4, CD34, CD13, CD29, CD41, CD44, CD73, CD90, CD105, stem cell factor, STRO-1, SSEA-3, CD133, CD15, CD38, glycophorin A (CD235a), CD2, CD3, CD4, CD5, CD7, CD8, CD10, CD11b, CD13, CD16, CD19, CD20, CD21, CD22, CD29, CD33, CD36, CD41, CD61, CD62E, CD72, CD73, CD90, HLA-DR, CD102, CD105, or hepatocyte growth factor receptor, or intracellular serum albumin. An antibody can be detectably labeled (e.g., fluorescently or enzymatically).

The invention is further described in the following examples, which do not limit the scope of the invention described in the claims.

EXAMPLES

Example 1

Separating Blood Cells

This example describes the general method by which cells were separated using the cell separation reagents described below. Equal volumes of a cell separation reagent (see Table 1) and an acid citrate dextrose (ACD), CPDA (citrate, phosphate, dextrose, adenine) or heparinized umbilical cord blood sample were combined (25 ml each) in a sterile closed container (e.g., a 50 ml conical tube). Samples containing white blood cell counts greater than $20 \times 10^6$ cells/ml were combined one part blood with two parts cell separation reagent. Tubes were gently mixed on a rocker platform for 20 to 45 minutes at room temperature. Tubes were stood upright in a rack for 30 to 50 minutes to permit agglutinated cells to partition away from unagglutinated cells, which remained in solution. A pipette was used to recover unagglutinated cells from the supernatant without disturbing the agglutinate. Recovered cells were washed in 25 ml PBS and centrifuged at 500×g for 7 minutes. The cell pellet was resuspended in 4 ml PBS+2% human serum albumin.

TABLE 1

Cell Separation Reagent

| | |
|---|---|
| Dextran (average molecular weight 413,000) | 20 g/l |
| Dulbecco's phosphate buffered saline (10×) | 100 ml/l |
| Sodium Heparin (10,000 units/ml) | 1 ml/l |
| Hank's balanced salt solution (pH 7.2-7.4) | 50 ml/l |
| Anti-human glycophorin A (murine IgM monoclonal antibody, clone 2.2.2.E7) | 0.1-15 mg/L (preferably about 0.25 mg/L) |
| Anti-CD15 (murine IgM monoclonal antibody, clone 324.3.B9) | 0.1-15 mg/L (preferably about 2.0 mg/L) |
| Anti-CD9 (murine IgM monoclonal antibody, clone 8.10.E7) | 0.1-15 mg/L (preferably about 2.0 mg/L) |

Cells also were recovered from the agglutinate using a hypotonic lysing solution containing EDTA and ethylene glycol-bis(2-aminoethylether)-N,N,N',N'-tetraacetic acid (EGTA). Agglutinated cells were treated with 25 ml VitaLyse® (BioE, St. Paul, Minn.) and vortexed. After 10 minutes, cells were centrifuged at 500×g for 7 minutes and the supernatant was removed. Cells were resuspended in 4 ml PBS.

Recoveries of erythrocytes, leukocytes, lymphocytes, monocytes, granulocytes, T cells, B cells, NK cells, hematopoietic stem cells, and non-hematopoietic stem cells were determined by standard flow cytometry and immunophenotyping. Prior to flow cytometry, leukocyte recovery (i.e., white blood cell count) was determined using a Coulter Onyx Hematology Analyzer. Cell types were identified and enumerated by combining hematology analysis with flow cytometry analysis, identifying cells on the basis of light scattering properties and staining by labeled antibodies.

As shown in Table 2, 99.9% of erythrocytes were removed, 99.8% monocytes and granulocytes, 74% of B cells, 64.9% of NK cells, and 99.4% of the platelets were removed from the cord blood.

TABLE 2

Recovery of Cells

| | Before separation | After separation |
|---|---|---|
| Erythrocytes per ml | $4.41 \times 10^9$ | $0.006 \times 10^9$ |
| Leukocytes per ml | $5.9 \times 10^6$ | $1.53 \times 10^6$ |
| Lymphocytes (%) | 28.7 | 99.0 |
| Monocytes (%) | 8.69 | 0.12 |
| Granulocytes (%) | 62.5 | .083 |
| T Cells (CD3+) | 19.7 | 83.2 |
| B Cells (CD19+) | 4.46 | 8.10 |
| NK Cells (CD16+) | 3.15 | 8.43 |
| Platelets per ml | $226 \times 10^6$ | $1.4 \times 10^6$ |

Example 2

Purification of MLPC

The cell separation reagent of Table 3 was used to isolate MLPC from the non-agglutinated supernatant phase. See FIG. 1 for a schematic of the purification.

TABLE 3

Cell Separation Reagent

| | |
|---|---|
| Dextran (average molecular weight 413,000) | 20 g/l |
| Dulbecco's phosphate buffered saline (10×) | 100 ml/l |
| Sodium Heparin (10,000 units/ml) | 1 ml/l |
| Hank's balanced salt solution (pH 7.2-7.4) | 50 ml/l |
| Anti-human glycophorin A (murine IgM monoclonal antibody, clone 2.2.2.E7) | 0.1-15 mg/L (preferably about 0.25 mg/L) |
| Anti-CD15 (murine IgM monoclonal antibody, clone 324.3.B9) | 0.1-15 mg/L (preferably about 2.0 mg/L) |
| Anti-CD9 (murine IgM monoclonal antibody, clone 8.10.E7) | 0.1-15 mg/L (preferably about 2.0 mg/L) |

Briefly, 50-150 ml of CPDA anti-coagulated umbilical cord blood (<48 hours old) was gently mixed with an equal volume of cell separation composition described in Table 3 for 30 minutes. After mixing was complete, the container holding the blood/cell separation composition mixture was placed in an upright position and the contents allowed to settle by normal 1×g gravity for 30 minutes. After settling was complete, the non-agglutinated cells were collected from the supernatant. The cells were recovered from the supernatant by centrifugation then washed with PBS. Cells were resuspended in complete MSCGM™ (Mesenchymal stem cell growth medium, catalog # PT-3001, Cambrex, Walkersville, Md.) and adjusted to $2-9 \times 10^6$ cells/ml with complete MSCGM™. Cells were plated in a standard plastic tissue culture flask (e.g., Corning), chambered slide, or other culture device and allowed to incubate overnight at 37° C. in a 5% $CO_2$ humidified atmosphere. All subsequent incubations were performed at 37° C. in a 5% $CO_2$ humidified atmosphere unless otherwise noted. MLPC attached to the plastic during this initial incubation. Non-adherent cells (T-cells, NK-cells and CD34+hematopoietic stem cells) were removed by vigorous washing of the flask or well with complete MSCGM™.

MLPC cultures were fed periodically by removal of the complete MSCGM™ and addition of fresh complete MSCGM™. Cell were maintained at concentrations of $1\times10^5$-$1\times10^6$ cells/75 cm$^2$ by this method. When cell cultures reached a concentration of $8\times10^5$-$1\times10^6$ cells/75 cm$^2$, cells were cryopreserved using 10% DMSO and 90% serum or expanded into new flasks. Cells were recovered from the adherent cultures by removal of the complete MSCGM™ and replacement with PBS+0.1% EGTA. Cells were incubated for 15-60 minutes at 37° C. then collected from the flask and washed in complete MSCGM™. Cells were then replated at $1\times10^5$ cells/mL. Cultures that were allowed to achieve confluency where found to have diminished capacity for both proliferation and differentiation. Subsequent to this finding, cultures were not allowed to achieve higher densities than $1\times10^6$ cells/75 cm$^2$.

Example 3

Morphology of MLPC and Development to Fibroblastic Morphology

Cord blood derived MLPC isolated and cultured according to Examples 1 and 2 were cultured in standard MSCGM™ until confluency. Depending on the donor, MLPC cultures achieved confluency in 2-8 weeks. The morphology of these cells during growth and cultural maturation is shown in FIGS. 2A-2D.

In the early stage shown in FIG. 2A, the cells are dividing very slowly and resemble circulating leukocytes but with dendritic cytoplasmic extensions. Many cells still exhibit the small round cell morphology that these cells would exhibit in circulation. As culture continues, the leukocyte-like cells start to change their morphology from the leukocyte-like appearance to a flatter, darker more fibroblast-like appearance (see FIG. 2B). When cells are dividing, they round up, divide, and then reattach to the culture vessel surface and spread out again. This slowly continues until the cells fill the available surface. FIG. 2C shows the morphology of cell cultures during logarithmic growth. FIG. 2D shows the morphology of a fully confluent culture of MLPC. With the exception of the two cells in active division seen in the lower left corner of the picture, all of the cells have a fibroblast-like morphology.

In summary, early during culture, cells appeared small and round, but had cytoplasmic projections, both finger-like and highly elongate projections, which help distinguish them from the other blood cells. Shortly after the initiation of the culture, the cells began to spread and flatten, taking on a morphology consistent with fibroblasts. Eventually, upon confluency, the cells grew in largely parallel orientation. Repeated growth of cultures to confluency resulted in their having diminished proliferation and differentiating capacity.

Example 4

Immunophenotyping of Cells by Immunofluorescent Microscopy

In order to determine the surface markers present on MLPC, freshly isolated cells were plated in 16 well chamber slides and grown to confluency. At various times during the culture (from 3 days post plating to post confluency), cells were harvested and stained for the following markers: CD45-FITC (BD/Pharmingen), CD34-PE (BD/Pharmingen), CD4-PE (BioE), CD8-PE (BioE), anti-HLA-DR-PE (BioE), CD41-PE (BioE), CD9-PE (Ancell), CD105-PE (Ancell), CD29-PE (Coulter), CD73-PE (BD/Pharmingen), CD90-PE (BD/Pharmingen), anti-hu Stem Cell Factor-FITC (R&D Systems), CD14-PE (BD/Pharmingen), CD15-FITC (Ancell), CD38-PE (BD/Pharmingen), CD2-PE (BD/Pharmingen), CD3-FITC (BD/Pharmingen), CD5-PE (BD/Pharmingen), CD7-PE (BD/Pharmingen), CD16-PE (BD/Pharmingen), CD20-FITC (BD/Pharmingen), CD22-FITC (BD/Pharmingen), CD 19-PE (BD/Pharmingen), CD33-PE (BD/Pharmingen), CD10-FITC (BD/Pharmingen), CD61-FITC (BD/Pharmingen), CD133-PE (R&D Systems), anti-STRO-1 (R&D Systems) and Goat anti-mouse IgG (H+ L)-PE (BioE), SSEA-3 (R&D Systems) and goat anti-rat IgG (H+ L)-PE (BioE), SSEA-4 (R&D Systems) and goat anti-mouse IgG (H+ L)-PE (BioE). The cell surface markers also were assessed in bone marrow MSC (Cambrex, Walkersville, Md.) and cord blood HSC (obtained from the non-adherent cells described above).

Briefly, cell culture medium was removed from the wells and the cells were washed 3× with Hank's Balanced Salt Solution+2% BSA. Cells were then stained with the antibodies for 20 minutes in the dark at room temperature. After incubation, the cells were washed 3× with Hank's Balanced Salt Solution+2% BSA and the cells were directly observed for fluorescence by fluorescent microscopy. Results obtained comparing cord blood derived MLPC with bone marrow-derived MSC's and cord blood derived hematopoietic stem cells (HSC) are outlined in Table 4.

TABLE 4

| Cell Marker | Early MLPC (Leukocyte morphology) | Mature MLPC (Fibroblast morphology) | Cord Blood HSC | Bone Marrow MSC |
|---|---|---|---|---|
| CD2 | Negative | Negative | Negative | Negative |
| CD3 | Negative | Negative | Negative | Negative |
| CD4 | Negative | Negative | Negative | Negative |
| CD5 | Negative | Negative | Negative | Negative |
| CD7 | Negative | Negative | Negative | Negative |
| CD8 | Negative | Negative | Negative | Negative |
| CD9 | Positive | Positive | Negative | Negative |
| CD10 | Negative | Negative | Negative | Negative |
| CD13 | Positive | Positive | Negative | Positive |
| CD14 | Negative | Negative | Negative | Negative |
| CD15 | Negative | Negative | Negative | Negative |
| CD16 | Negative | Negative | Negative | Negative |
| CD19 | Negative | Negative | Negative | Negative |
| CD20 | Negative | Negative | Negative | Negative |
| CD22 | Negative | Negative | Negative | Negative |
| CD29 | Positive | Positive | Positive | Positive |
| CD33 | Negative | Negative | Variable | Negative |
| CD34 | Positive | Negative | Positive | Negative |
| CD36 | Negative | Negative | Negative | Negative |
| CD38 | Negative | Negative | Variable | Negative |
| CD41 | Negative | Negative | Negative | Negative |
| CD45 | Positive | Negative | Positive | Negative |
| CD61 | Negative | Negative | Variable | Negative |
| CD73 | Positive | Positive | Negative | Positive |
| Anti-HLA-DR | Negative | Negative | Variable | Negative |
| CD90 | Positive | Positive | Positive | Positive |
| CD105 | Positive | Positive | Negative | Positive |
| STRO-1 | Positive | Negative | Negative | Negative |
| SSEA-3 | Positive | Negative | Negative | Negative |
| SSEA-4 | Positive | Negative | Negative | Negative |
| SCF | Positive | Negative | Negative | Negative |
| Glycophorin A | Negative | Negative | Negative | Negative |
| CD133 | Positive | Negative | Positive | Negative |

Example 5

Clonal MLPC Cell Lines

After the second passage of MLPC cultures from Example 2, the cells were detached from the plastic surface of the culture vessel by substituting PBS containing 0.1% EGTA (pH 7.3) for the cell culture medium. The cells were diluted to a concentration of 1.3 cells/ml in complete MSCGM™ and distributed into a 96 well culture plate at a volume of 0.2 ml/well, resulting in an average distribution of approximately 1 cell/3 wells. After allowing the cells to attach to the plate by overnight incubation at 37° C., the plate was scored for actual distribution. Only the wells with 1 cell/well were followed for growth. As the cells multiplied and achieved concentrations of $1-5\times10^5$ cells/75 cm$^2$, they were transferred to a larger culture vessel in order to maintain the cells at a concentration between $1\times10^5$ and $5\times10^5$ cells/75 cm$^2$ to maintain logarithmic growth. Cells were cultured at 37° C. in a 5% $CO_2$ atmosphere.

At least 52 clonal cell lines have been established using this procedure and were designated: UM081704-1-E2, UM081704-1-B6, UM081704-1-G11, UM081704-1-G9, UM081704-1-E9, UM081704-1-E11, UM081704-1-G8, UM081704-1-H3, UM081704-1-D6, UM081704-1-H11, UM081704-1-B4, UM081704-1-H4, UM081704-1-C2, UM081704-1-G1, UM081704-1-E10, UM081704-1-B7, UM081704-1-G4, UM081704-1-F12, UM081704-1-H1, UM081704-1-D3, UM081704-1-A2, UM081704-1-B11, UM081704-1-D5, UM081704-1-E4, UM081704-1-C10, UM081704-1-A5, UM081704-1-E8, UM081704-1-C12, UM081704-1-E5, UM081704-1-A12, UM081704-1-C5, UM081704-1-A4, UM081704-1-A3, MH091404-2 #1-1.G10, UM093004-1-A3, UM093004-1-B7, UM093004-1-F2, UM093004-1-A12, UM093004-1-G11, UM093004-1-G4, UM093004-1-B12, UM093004-2-A6, UM093004-2-A9, UM093004-2-B9, UM093004-2-C5, UM093004-2-D12, UM093004-2-H3, UM093004-2-H11, UM093004-2-H4, UM093004-2-A5, UM093004-2-C3, and UM093004-2-C10. The surface markers of clonal cell line UM081704-1-E8 were assessed according to the procedure outlined in Example 4 and found to be the same as the "mature MLPC" having fibroblast morphology, as shown in Table 4.

Example 6

Osteocytic Differentiation of MLPC

A population of MLPC and clonal cell line UM081704-1-E8 each were cultured in complete MSCGMT™ and grown under logarithmic growth conditions outlined above. Cells were harvested by treatment with PBS+0.1% EGTA and replated at $5\times10^3$ to $2\times10^4$/ml in complete MSCGM™. The cells were allowed to adhere overnight and then the medium was replaced with Osteogenic Differentiation Medium (catalog # PT-3002, Cambrex,) consisting of complete MSCGM™ supplemented with dexamethasone, L-glutamine, ascorbate, and β-glycerophosphate. Cells were cultured at 37° C. in a 5% $CO_2$ atmosphere and fed every 3-4 days for 2-3 weeks. Deposition of calcium crystals was demonstrated by using a modification of the Alizarin red procedure and observing red staining of calcium mineralization by phase contrast and fluorescent microscopy.

Example 7

Adipocytic Differentiation of MLPC

A population of MLPC and clonal cell line UM081704-1-E8 each were plated in complete MSCGM™ at a concentration of $1\times10^4$ to $2\times10^5$ cells/mL medium and cultured at 37° C. in a 5% $CO_2$ atmosphere. Cells were allowed to re-adhere to the culture plate and were fed every 3-4 days until the cultures reached confluency. At 100% confluency, cells were differentiated by culture in Adipogenesis differentiation medium (catalog #PT-3004, Cambrex) consisting of complete MSCGM™ supplemented with hu-insulin, L-glutamine, dexamethasone, indomethacin, and 3-isobutyl-1-methyl-xanthine, for at least 14 days.

To assess differentiation, the cells were stained with Oil Red stain specific for lipid. Confluent cultures of MLPC display a fibroblast-like morphology and do not display any evidence of liposome development as assessed by Oil Red staining. In contrast, MLPC differentiated with Adipogenic medium for 3 weeks exhibit liposomes that are characteristic of adipocytes (i.e., bright white vessels in cytoplasm) and that stain red with the Oil Red stain. MLPC differentiated with Adipogenic medium also fluoresce green with Nile Red stain specific for trigycerides. Undifferentiated cells retain their fibroblast-like morphology and do not stain.

Example 8

Myocytic Differentiation of MLPC

MLPC (both a population and clonal cell line UM081704-1-E8) were plated in complete MSCGM™ at a concentration of $1.9\times10^4$ cells/well within a 4-chamber fibronectin pre-coated slide and allowed to attach to the plate for 24-48 hr at 37° C. in a 5% $CO_2$ atmosphere. Medium was removed and replaced with 10 μM 5-azacytidine (catalog #A1287, Sigma Chemical Co.) and incubated for 24 hours. Cells were washed twice with PBS and fed with SkGM™ Skeletal Muscle Cell Medium (catalog # CC-3160, Cambrex) containing recombinant human epidermal growth factor (huEGF), human insulin, Fetuin, dexamethasone, and recombinant human basic fibroblast growth factor (100 ng/mL) (huFGF-basic, catalog # F0291, Sigma Chemical Co., St. Louis, Mo.). Cells were fed every 2-3 days for approximately 21 days. Control wells were fed with MSCGM™ while experimental wells were fed with SkGM™ (as described above).

Cultures were harvested 7 days post initiation of myocytic culture. Culture supernatant was removed and cells were fixed for 2 hours with 2% buffered formalin. Cells were permeabilized with PermaCyte™ (BioE, St. Paul, Minn.) and stained with mouse monoclonal antibody specific for human fast skeletal myosin (MY-32, catalog #ab7784, Abcam, Cambridge, Mass.) or mouse monoclonal antibody specific for alpha actinin (BM 75.2, catalog #ab11008, Abcam). Cells were incubated with the primary antibody for 20 minutes, washed with PBS and counter stained with goat anti-mouse IgG (H+L)-PE (BioE, St. Paul, Minn.). The myocytic culture contained fast skeletal muscle myosin and alpha actinin, which is indicative of the transdifferentiation of MLPC to skeletal muscle cells.

Example 9

Neurocytic Differentiation of MLPC

Bone marrow derived hMSC (Cambrex), cord blood MLPC, and MLPC clonal cell line were grown under logarithmic growth conditions described above. Cells were harvested as described above and replated at 0.8×10⁴ cells per chamber in 4-chamber slides that were pre-coated with poly-D-lysine and laminin (BD Biosciences Discovery Labware, catalog #354688) in 0.5 mL of NPMM™ (catalog #CC-3209, Cambrex) containing huFGF-basic, huEGF, brain-derived neurotrophic factor, neural survival factor-1, fibroblast growth factor-4 (20 ng/mL), and 200 mM GlutaMax I Supplement (catalog #35050-061, Invitrogen, Carlsbad, Calif.). The medium was changed every 2-3 days for 21 days. Neurospheres developed after 4 to 20 days. Transformation of MLPC to neural lineage was confirmed by positive staining for nestin (monoclonal anti-human nestin antibody, MAB1259, clone 196908, R&D Systems), class III beta-tubulin (tubulin b-4) (monoclonal anti-neuron-specific class III beta-tubulin antibody, MAB1195, Clone TuJ-1, R&D Systems), glial fibrillary acidic protein (GFAP) (monoclonal anti-human GFAP, HG2b-GF5, clone GF5, Advanced Immunochemical, Inc.), and galactocerebroside (GalC) (mouse anti-human GalC monoclonal antibody MAB342, clone mGalC, Chemicon).

Cells were further differentiated into neurons by the addition of 10 ng/mL BDNF (catalog #B3795, Sigma Chemical Co.) and 10 ng/mL NT3 (catalog #N1905, Sigma Chemical Co.) to the neural progenitor maintenance medium and further culturing for 10-14 days. Neurospheres were further differentiated into astrocytes by the addition of $10^{-6}$ M retinoic acid (catalog #R2625, Sigma Chemical Co.), 10 ng/mL LIF (catalog #L5158, Sigma Chemical Co.) and 10 ng/mL CNTF (catalog #C3710, Sigma Chemical Co.) to the neural progenitor maintenance medium and further culturing for 10-14 days. Neurospheres were further differentiated into oligodendrocytes by the addition of $10^{-6}$ M T3 (catalog #T5516, Sigma Chemical Co.) to the neural progenitor maintenance medium and further culturing for 10-14 days. Differentiation to oligodendrocytes was confirmed by positive staining for myelin basic protein (MBP) (monoclonal anti-MBP, catalog #ab8764, clone B505, Abcam).

Example 10

Endothelial Differentiation of MLPC

MLPC were plated at 1.9×10⁴ cells per well within a 4-chamber slide (2 cm²). Cells were fed with 1 ml of endothelial growth medium-microvasculature (EGM™-MV, catalog #CC-3125, Cambrex) containing heparin, bovine brain extract, human recombinant epithelial growth factor and hydrocortisone. The cells were fed by changing the medium every 2-3 days for approximately 21 days. Morphological changes occurred within 7-10 days. Differentiation of MLPC's to endothelial lineage was assessed by staining for CD62E [E-selectin, mouse anti-human CD62E monoclonal antibody, catalog #551145, clone 68-5H11, BD Pharmingen] and CD102 [ICAM-2, monoclonal anti-human ICAM-2, MAB244, clone 86911, R&D Systems], CD34 [BD Pharmingen] and STRO-1 (R&D Systems]. Control MLPC cultures grown in MSCGM for 14 days were negative for CD62E staining and CD102, CD34 and STRO-1, while differentiated cultures were positive for both CD62E, CD102, CD34, and STRO-1.

Example 11

Differentiation of MLPC into Hepatocyte/Pancreatic Precursor Cells

MLPC were plated at a concentration of 1×10⁵ cells/cm² in vitro in HCM™ medium (catalog #CC-3198, Cambrex) containing ascorbic acid, hydrocortisone, transferrin, insulin, huEGF, recombinant human hepatocyte growth factor (40 ng/mL), huFGF-basic (20 ng/mL), recombinant human FGF-4 (20 ng/mL), and stem cell factor (40 ng/mL). Cells were cultured for 29 or more days to induce differentiation to precursor cells of both hepatocytes and pancreatic cells lineage. MLPC changed from a fibroblast morphology to a hepatocyte morphology, expressed cell surface receptors for Hepatocyte Growth Factor, and produced both human serum albumin, a cellular product of hepatocytes, and insulin, a cellular product of pancreatic islet cells, both confirmed by intracellular antibody staining on day 30.

Example 12

Differentiation of MLPC into Hepatocytes

Nineteen thousand MLPC of clonal line UM081704-1-C3 in 100 µl of MSCGM™ were loaded into a three-dimensional collagen composite scaffold (BD Biosciences, catalog #354613) and then grown in MSCGM™. After 7 days in MSCGM™, the medium was exchanged for HCM™ (catalog #CC-3198, Cambrex) containing ascorbic acid, hydrocortisone, transferrin, insulin, huEGF, recombinant human hepatocyte growth factor (40 ng/mL), huFGF-basic (20 ng/mL), recombinant human FGF-4 (20 ng/mL), and stem cell factor (40 ng/mL). Cells were allowed to grow for an additional 40 days. Cells within the collagen scaffold and those that overgrew into the well of the culture vessel demonstrated morphology consistent with mature hepatocytes and expressed cell surface receptors for hepatocyte growth factor and high levels of intracellular serum albumin. The absence of expression of intracellular insulin and proinsulin demonstrate the differentiation of the MLPC past the common precursor for hepatocytes and pancreatic beta cells.

Scaffolds loaded with the developed hepatocytes were cryopreserved by exchanging the growth medium with 10% DMSO in fetal bovine serum (freeze medium). Cryovials containing one scaffold and 0.5 mL of freeze medium were frozen overnight at −85° C. in an alcohol bath after which the vial was transferred to liquid nitrogen for long term storage. Cells can be recovered from cryopreservation by quickly thawing the frozen vial and transferring the hepatocyte-loaded scaffold to a well or tissue culture flask. Sufficient hepatocyte growth medium (e.g., as described above) can be added to completely submerge the scaffold and then the cells can be cultured under standard conditions (i.e., 37° C. in a 5% $CO_2$ atmosphere). Cells can be recovered from the collagen scaffold by incubation in 1 mL of collagenase (300 U/ml) (Sigma catalog# C-0773) in serum-free culture medium (SFPF, Sigma catalog# S-2897) at 37° C. for one hour. Cells then can be transferred to another tissue culture vessel or loaded onto a new scaffold. Cells in this format can be used for transplantation to animal models for functionality studies, re-cultured in vitro or used directly in P450 assays such as the CYP3A4/BQ assay (BD Bioscience, San Jose, Calif., catalog #459110).

Other Embodiments

While the invention has been described in conjunction with the foregoing detailed description and examples, the foregoing description and examples are intended to illustrate and not to limit the scope of the invention, which is defined by the scope of the appended claims. Other aspects, advantages, and modifications are within the scope of the claims.

What is claimed is:

1. A method of producing a population of cells having a mature hepatocyte phenotype, said method comprising a) providing a three-dimensional scaffold housing a purified population of multi-lineage progenitor cells (MLPC) or a clonal line of MLPC; and culturing said purified population of MLPC or said clonal line of MLPC with a differentiation medium effective to induce differentiation of said MLPC into cells having said mature hepatocyte phenotype, wherein said MLPC within said purified population are positive for CD9, CD13, CD29, CD44, CD73, CD90 and CD105, and negative for CD10, CD34, CD41, CD45, Stro-1, SSEA-3, and SSEA-4, and wherein said mature hepatocyte phenotype comprises the presence of hepatocyte growth factor receptor and intracellular human serum albumin and the absence of intracellular pancreas-associated insulin and proinsulin production.

2. The method of claim 1, wherein said differentiation medium comprises ascorbic acid, hydrocortisone, transferrin, insulin, epidermal growth factor, hepatocyte growth factor, fibroblast growth factor-basic, fibroblast growth factor-4, and stem cell factor.

3. The method of claim 1, wherein said three-dimensional scaffold comprises collagen.

4. The method of claim 1, wherein said three-dimensional scaffold is coated with collagen.

5. The method of claim 1, said method further comprising testing said cells having said mature hepatocyte phenotype for intracellular serum albumin or hepatocyte growth factor receptor.

6. The method of claim 5, said method further comprising testing said cells for intracellular insulin or intracellular proinsulin.

* * * * *